US010413558B2

(12) United States Patent
Zeicher

(10) Patent No.: US 10,413,558 B2
(45) Date of Patent: Sep. 17, 2019

(54) MULTI-INGREDIENT PHARMACEUTICAL COMPOSITION FOR USE IN CANCER THERAPY

(71) Applicant: TARGETED THERAPIES RESEARCH AND CONSULTING CENTRE SPRL (TTRCC), Uccle (BE)

(72) Inventor: Marc Zeicher, Uccle (BE)

(73) Assignee: TARGETED THERAPIES RESEARCH AND CONSULTING CENTER SPRL, Uccle (BE)

( * ) Notice: Subject to any disclaimer, the term of this patent is extended or adjusted under 35 U.S.C. 154(b) by 44 days.

(21) Appl. No.: 15/518,636

(22) PCT Filed: Oct. 19, 2015

(86) PCT No.: PCT/EP2015/074092
§ 371 (c)(1),
(2) Date: Apr. 12, 2017

(87) PCT Pub. No.: WO2016/059247
PCT Pub. Date: Apr. 21, 2016

(65) Prior Publication Data
US 2017/0232008 A1    Aug. 17, 2017

(30) Foreign Application Priority Data
Oct. 17, 2014   (EP) .................................... 14189304

(51) Int. Cl.
| | |
|---|---|
| *A61K 31/593* | (2006.01) |
| *A61K 31/4045* | (2006.01) |
| *A61K 31/12* | (2006.01) |
| *A61K 31/4706* | (2006.01) |
| *A61K 31/55* | (2006.01) |
| *A61K 31/415* | (2006.01) |
| *A61K 31/5377* | (2006.01) |
| *A61K 31/4439* | (2006.01) |
| *A61K 31/40* | (2006.01) |
| *A61K 45/06* | (2006.01) |
| *A61K 31/155* | (2006.01) |
| *A61K 31/20* | (2006.01) |
| *A61K 31/22* | (2006.01) |
| *A61K 31/366* | (2006.01) |
| *A61K 31/405* | (2006.01) |
| *A61K 31/47* | (2006.01) |
| *A61K 31/505* | (2006.01) |
| *A61K 31/65* | (2006.01) |
| *A61K 31/66* | (2006.01) |
| *A61K 31/145* | (2006.01) |

(52) U.S. Cl.
CPC ............ *A61K 31/593* (2013.01); *A61K 31/12* (2013.01); *A61K 31/145* (2013.01); *A61K 31/155* (2013.01); *A61K 31/20* (2013.01); *A61K 31/22* (2013.01); *A61K 31/366* (2013.01); *A61K 31/40* (2013.01); *A61K 31/405* (2013.01); *A61K 31/4045* (2013.01); *A61K 31/4439* (2013.01); *A61K 31/47* (2013.01); *A61K 31/4706* (2013.01); *A61K 31/505* (2013.01); *A61K 31/5377* (2013.01); *A61K 31/65* (2013.01); *A61K 31/66* (2013.01); *A61K 45/06* (2013.01)

(58) Field of Classification Search
CPC .. A61K 31/593; A61K 31/4045; A61K 31/12; A61K 31/4706; A61K 31/55; A61K 31/415; A61K 31/5377; A61K 31/4439; A61K 31/40
USPC ....... 514/154, 167, 338, 415, 460, 557, 638, 514/679
See application file for complete search history.

(56) References Cited

U.S. PATENT DOCUMENTS

2014/0170211 A1*   6/2014   Bennett .................. A61K 36/16
424/451

FOREIGN PATENT DOCUMENTS

WO   2012122295   9/2012

OTHER PUBLICATIONS

Proietti Sara et al: "Melatonin and vitamin D-3 synergistically down-regulate Akt and MDM2 leading to TGF beta-1-dependent growth inhibition of breast cancer cells", Journal of Pineal Research, vol. 50, No. 2, Mar. 2011 (Mar. 1, 2011), pp. 150-158, XP055175667.
Bizzarri Mariano et al: "Melatonin and vitamin D3 increase TGF-beta1 release and induce growth inhibition in breast cancer cell cultures.", Journal of Surgical Research, vol. 110, No. 2, Apr. 2003 (Apr. 1, 2003), pp. 332-337, XP002737323, ISSN: 0022-4804.
Liu Yuhong et al: "Synergistic effects of curcumin on ALL-trans retinoic acid- and 1-alpha,25-dihydroxyvitamin D-3-induced differentiation in human promyelocytic leukemia HL-60 cells", Oncology Research, vol. 9, No. 1, 1997, pp. 19-29, XP008175410, ISSN: 0965-0407.
Danilenko Michael et al: "Enhancement by other compounds of the anti-cancer activity of vitamin D3 and its analogs", Experimental Cell Research, Academic Press, US, vol. 298, No. 2, Aug. 15, 2004 (Aug. 15, 2004), pp. 339-358, XP002509129, ISSN: 0014-4827, [retrieved on May 25, 2004], DOI: 10.1016/J.YEXCR.2004.04.029.
Di Bella G et al: "Melatonin anticancer effects: Review", International Journal of Molecular Sciences 2013 MDPI AG CHE, vol. 14, No. 2, Feb. 2013 (Feb. 1, 2013), pp. 2410-2430, XP002737324, ISSN: 1661-6596.
Hoque Ashraful et al: "Statin induces apoptosis and cell growth arrest in prostate cancer cells", Cancer Epidemiology Biomarkers & Prevention, vol. 17, No, 1, Jan. 2008 (Jan. 1, 2008), pp. 88-94, XP055176005, ISSN: 1055-9965.
Miwa Hiroshi et al: "Different Ways of Apoptosis Observed in Leukemia Cell Lines Induced by HMG-CoA Reductase Inhibitor, Cerivastatin.", Blood, vol. 100, No. 11, Nov. 16, 2002 (Nov. 16, 2002), & 44th Annual Meeting of the American Society of Hematology; Philadelphia, PA, USA; Dec. 6-10, 2002, XP008175424, ISSN: 0006-4971.

* cited by examiner

Primary Examiner — Raymond J Henley, III
(74) Attorney, Agent, or Firm — Duane Morris LLP; J. Rodman Steele, Jr.; Gregory M. Lefkowitz

(57) ABSTRACT

A pharmaceutical composition or kit of parts comprising at least three ingredients from a HMG-CoA reductase inhibitor, a leukotriene antagonist, a proton pump inhibitor, melatonin or a melatonin receptor agonist, a bioavailable preparation of a curcuminoid, a calciferol derivative, a compound from the group consisting of metformin and phenformin, valproate, minocycline and chloroquine and one or more pharmaceutically acceptable carriers or excipients.

20 Claims, 1 Drawing Sheet

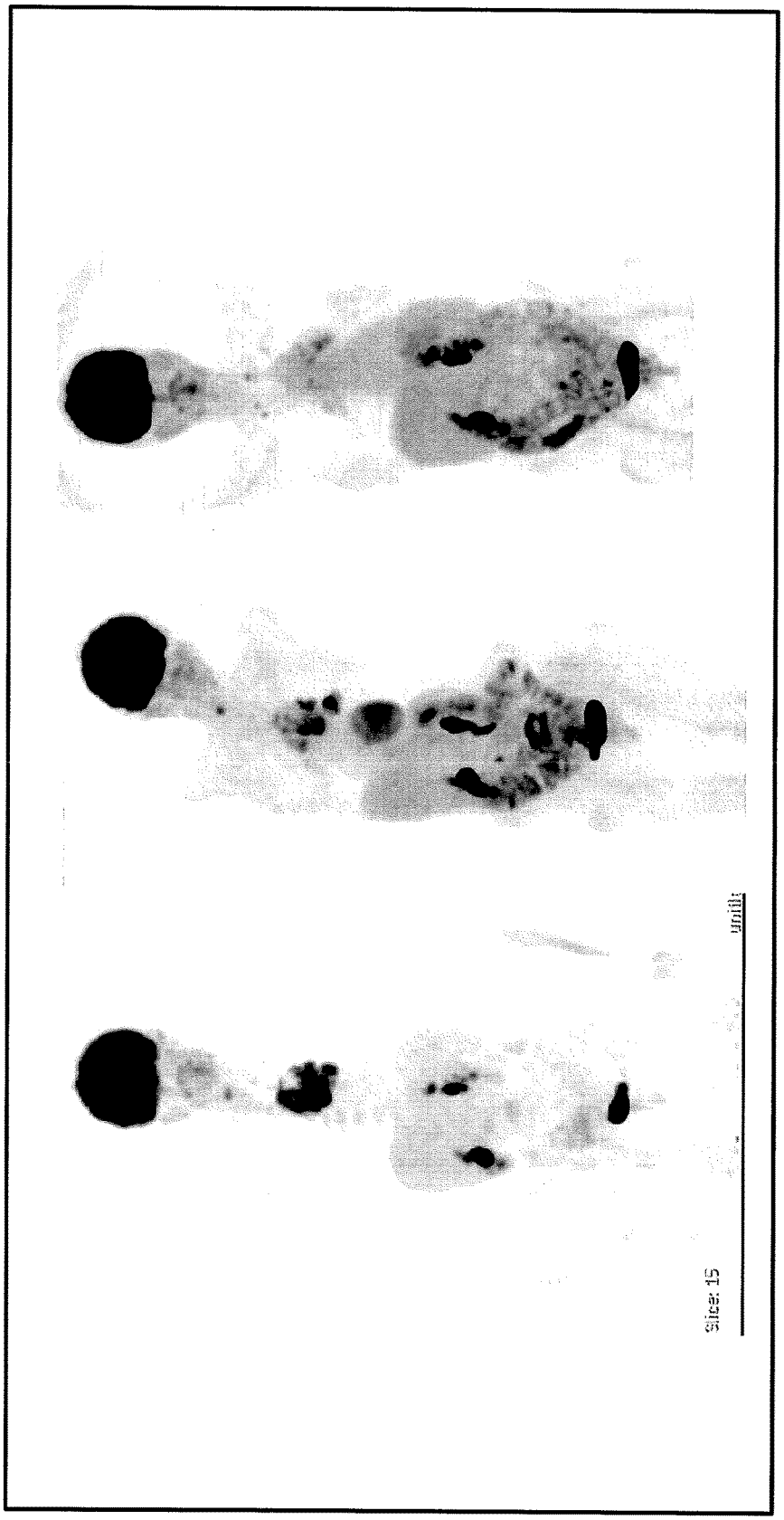

MULTI-INGREDIENT PHARMACEUTICAL COMPOSITION FOR USE IN CANCER THERAPY

CROSS-REFERENCE TO RELATED APPLICATIONS

This application is a § 371 national stage entry of International Application No. PCT/EP2015/074092, filed Oct. 19, 2015, which claims priority to European Patent Application No. 14189304.0, filed Oct. 17, 2014, the entire contents of which is incorporated herein by reference.

TECHNICAL FIELD OF THE INVENTION

The present invention relates to a multi-ingredient pharmaceutical composition for administration to a patient for use in the prevention or treatment of cancer.

BACKGROUND OF THE INVENTION

In spite of major advances in oncology, the World Health Organization predicts that cancer incidence will double within the next two decades. Although it is well understood that cancer is a hyperproliferative disorder mediated through dysregulation of multiple cell signaling pathways, most cancer drug development remains focused on modulation of specific targets, mostly one at a time, with agents referred to as "targeted therapies," "smart drugs," or "magic bullets." How many cancer targets there are is not known, and how many targets must be attacked to control cancer growth is not well understood.

A cancer may have as many as 500 different dysregulated genes. The dysregulation of various genes may occur over a period as long as 20-30 years before a given cancer begins to manifest its symptoms. Therefore, targeting or inhibiting a single gene product or cell signaling pathway is unlikely to prevent or destroy cancer. Chemotherapy and specific targeted drugs have been developed to disrupt these gene products or pathways, thereby inducing cell death and impeding progression of malignant changes in cells. However, problems such as ineffective targeting and drug resistance have plagued these agents, necessitating changes in the approach to systemic cancer therapy. The current paradigm of cancer chemotherapy is either combinations of several drugs or a drug that modulates multiple targets. The combination chemotherapy approach uses drugs with different mechanisms of action to increase cancer killing. Various drugs that modulate multiple targets, have been approved by the U.S. Food and Drug Administration (FDA) for treatment of various cancer types. However, these drugs are costly, have a long list of undesirable side effects, and most of them are still not effective enough to have a significant effect on the course of the disease.

Targeted therapies should attack simultaneously different pathways in order to be more efficient. In practice, this goal is difficult to achieve for several reasons: new drugs are extremely expensive, their full pattern of side-effects and interference is incompletely known and it is difficult to get different drug companies to cooperate in combination clinical trials. Moreover, regulatory authorities (FDA and EMEA) require that a new drug proves its efficacy in monotherapy clinical trials and hence synergy of two drugs, which on their own are ineffective, is missed. On the other hand, there is broad recognition that multiple cross-covering growth promoting signaling pathways and cell death avoiding mechanisms are active in cancer cells. On the basis of pre-clinical results, there have been some attempts to treat cancer patients with compositions including melatonin and calciferol derivatives. However, these two molecules together did not show sufficient efficacy in clinical trials or only showed some effect in association to many other compounds, including chemotherapeutic drugs. Similarly, curcumin has been considered as anticancer agent. However, the required blood levels were of 10 μM, which is nearly impossible to obtain in human clinical condition.

SUMMARY OF THE INVENTION

The present invention relates to a pharmaceutical composition or a pharmaceutical kit of part comprising a calciferol derivative, melatonin and one or more compounds selected from the group consisting of curcumin, an HMG-CoA reductase inhibitor, a proton pump inhibitor, metformin, phenformin, valproate, minocycline and chloroquine.

Alternatively, the present invention relates to a pharmaceutical composition or a pharmaceutical kit of part comprising, a calciferol derivative, curcumin and one or more compounds selected from the group consisting of melatonin, an HMG-CoA reductase inhibitor, a proton pump inhibitor, metformin, phenformin, valproate, minocycline and chloroquine.

Advantageously, the present invention relates to a pharmaceutical composition or a pharmaceutical kit of part comprising, a calciferol derivative, melatonin, curcumin and one or more compounds selected from the group consisting of an HMG-CoA reductase inhibitor, a proton pump inhibitor, metformin, phenformin, valproate, minocycline and chloroquine.

Preferably, the pharmaceutical composition or the pharmaceutical kit of the present invention comprises melatonin and/or curcumin, a calciferol derivative, an HMG-CoA reductase inhibitor, and one or more compounds selected from the group consisting of a proton pump inhibitor, metformin, phenformin, valproate, minocycline and chloroquine. Alternatively, the pharmaceutical composition or the pharmaceutical kit of the present invention comprises melatonin and/or curcumin, a calciferol derivative, a proton pump inhibitor, and one or more compounds selected from the group consisting of an HMG-CoA reductase inhibitor, metformin, phenformin, valproate, minocycline and chloroquine.

Preferably, these pharmaceutical compositions or kit of parts, further comprise a proteasome inhibitor such as disulfiram.

Preferably, these pharmaceutical compositions or kit of parts, especially those comprising chloroquine and/or disulfiram (or a proteasome inhibitor) further comprise a neurokinin-1 receptor antagonist like aprepitant.

Alternatively, the pharmaceutical composition or the pharmaceutical kit of the present invention comprises melatonin and/or curcumin, a calciferol derivative, chloroquine, and one or more compounds selected from the group consisting of an HMG-CoA reductase inhibitor, a proton pump inhibitor, metformin, phenformin, valproate and minocycline. Alternatively, the pharmaceutical composition or the pharmaceutical kit of the present invention comprises melatonin and/or curcumin, a calciferol derivative, metformin, and one or more compounds selected from the group consisting of an HMG-CoA reductase inhibitor, a proton pump inhibitor, chloroquine, valproate and minocycline; preferably, this pharmaceutical composition or the pharmaceutical kit of part is given to a patient as a sole therapy (with no additional chemotherapy).

Preferably, the pharmaceutical composition or the pharmaceutical kit of the present invention comprises melatonin and curcumin.

The pharmaceutical composition or the pharmaceutical kit of part of the present invention preferably further comprises a leukotriene antagonist.

Advantageously, pharmaceutical composition or the pharmaceutical kit of part of the present invention comprises between 10 mg and 100 mg/Day (d) of melatonin, and/or between 20 and 400 mg/d of curcumin and/or between 250 and 2000 mg/d of metformin, preferably wherein said curcumin is present in the said composition together with an at least 6-time mass excess of an edible emulsifier.

Preferably, the pharmaceutical composition or the pharmaceutical kit of the present invention comprises a calciferol derivative, melatonin, curcumin, metformin and another compound selected from the group consisting of an HMG-CoA reductase inhibitor, a proton pump inhibitor, valproate, minocycline and chloroquine, and possibly also aprepitant.

Preferably, the pharmaceutical composition or the pharmaceutical kit of the present invention comprises a calciferol derivative, melatonin, curcumin, metformin, an HMG-CoA reductase inhibitor and another compound selected from the group consisting of a proton pump inhibitor, valproate, minocycline and chloroquine, and possibly also aprepitant.

Possibly, the HMG-CoA reductase inhibitor of the pharmaceutical composition or the pharmaceutical kit of the present invention is selected from the group consisting of simvastatin, atorvastatin, fluvastatin, lovastatin, pitavastatin, pravastatin, and rosuvastatin.

Possibly, the proton pump inhibitor of the pharmaceutical composition or the pharmaceutical kit of part of the present invention is selected from the group consisting of omeprazole, lansoprazole, dexlansoprazole, esomeprazole, pantoprazole, rabeprazole and ilaprazole.

Possibly, the calciferol derivative of the pharmaceutical composition or the pharmaceutical kit of part of the present invention is selected from the group consisting of alfacalcidol, calcifediol, calcitriol, cholecalciferol, ergocalciferol, 22-dihydroergocalciferol and sitocalciferol.

The pharmaceutical composition or the pharmaceutical kit of part of the present invention is preferably for use in the treatment or the prevention of cancer, more preferably selected from the group consisting of brain cancer, breast cancer, cervical cancer, colon cancer, gastric cancer, kidney cancer, leukemia, liver cancer, lymphoma, lung cancer, ovarian cancer, pancreatic cancer, prostate cancer, rectal cancer, sarcoma, skin cancer, testicular cancer, or uterine cancer.

Alternatively, the pharmaceutical composition or the pharmaceutical kit of part of the present invention is for the prevention or the treatment (e.g. slowing the effects) of neurodegenerative diseases.

DETAILED DESCRIPTION OF THE INVENTION

Numerous molecular pathways operating differently in cancer and normal cells have been identified. There is a need for a new multi-ingredient pharmaceutical composition for use in the treatment of cancer. Many currently marketed drugs (for other indications than cancer) and nutraceuticals have been reported in in vitro screening of drug libraries, preclinical cancer animal models epidemiological data (incidence, survival), clinical trials (prevention, add-on therapy) as potentially interfering with these pathways. The inventor has treated cancer patients with a selected panel of drugs and nutraceuticals displaying antitumor properties and low toxicity. Such treatment is based on a calciferol derivative, melatonin and/or curcumin. One or several (or all of) additional compounds is preferably added, these additional compounds being selected from the group consisting of metformin, HMG-CoA reductase inhibitor, a proton pump inhibitor and a leukotriene antagonist. If needed, e.g. if the level of cancer biomarkers and/or tumor size are increasing, further compounds are added, selected from the group consisting of valproate (and/or valproic acid), minocycline (or doxycycline). Finally, if the treatment still shows poor anticancer efficacy, chloroquine and/or one or several other molecules of the present invention are added.

Such a basis treatment (at least three from the group consisting of calciferol derivative, melatonin and/or curcumin, metformin, HMG-CoA reductase inhibitor, a proton pump inhibitor and a leukotriene antagonist) has boosted the efficacy of the more toxic and expensive drugs and other therapies nowadays used in cancer therapy. In some patients, being given in absence of any other treatments, such treatment has demonstrated alone anticancer efficacy: the combination of carefully selected repurposed approved drugs by acting on different pathways of activation or repression interferes synergistically with tumour growth, apoptosis resistance and tumour-stroma interaction, angiogenesis, immunogenicity and cancer stem cells survival.

It is therefore an object of the present invention to provide a pharmaceutical composition for prophylactic use or for use in cancer therapy either as the sole therapy or as an adjunct to other modalities of cancer therapy such as chemotherapy, metronomic therapy, radiotherapy, surgery, hormonotherapy, immunotherapy, antiangiogenic, biological response modifiers and targeted therapy. An advantage of the present invention is that the long term health effects of the drugs and nutraceuticals in the cocktail of drugs and nutraceuticals of the present invention are known and well-characterised and are mild.

A further advantage of the present invention is that the long term or even permanent taking of a cocktail of drugs and nutraceuticals as a mean of obtaining remission from or limiting the effects of cancer represents an acceptable health risk.

A still further advantage of the present invention is the avoidance or reduction of side effects in cancer treatment, while including multiple repurposed drugs targeting multiple cancer progression pathways thereby increasing the probability of success in preventing cancer progression and killing cancer cells.

A still further advantage of the present invention is an increase in the potency of and tolerance for other prior, concurrent or subsequent cancer therapies.

A still further advantage is that the likelihood of resistance to any one agent developing in the treatment is strongly diminished.

According to a first aspect of the present invention discloses a pharmaceutical (human or veterinary) composition comprising at least three ingredients from a HMG-CoA reductase inhibitor, a leukotriene antagonist, a proton pump inhibitor, melatonin or a melatonin receptor agonist, (bio-available) curcumin, a calciferol derivative, metformin or phenformin, valproate or valproic acid, minocycline, doxycycline and chloroquine; and one or more pharmaceutically acceptable carriers or excipients, wherein at least two of said at least three ingredients is selected from a HMG-CoA reductase inhibitor, a proton pump inhibitor, melatonin or a melatonin receptor agonist, (bioavailable) curcumin, a calciferol derivative and a compound from the group consisting of metformin and phenformin, and possibly the third is selected from the group consisting of a leukotriene antagonist, valproate and/or valproic acid, minocycline, doxycycline, and chloroquine.

Advantageously, the present pharmaceutical composition comprises the calciferol derivative, (bioavailable) curcumin, and/or the melatonin (or melatonin receptor agonist) formulated in one bio-available composition (such as a capsule or a tablet). A preferred pharmaceutical composition (such as a capsule or a tablet) comprises a calciferol derivative, between 20 and 100 mg of curcumin, and possibly between 10 mg (preferably 20 mg) and 100 mg of melatonin, and this preferred pharmaceutical composition further comprises between 120 and 600 mg of an edible emulsifier, wherein the weight ratio of curcumin:emulsifier is of at least 3, preferably of at least 6 (but less than 20, preferably less than 10) and wherein the edible emulsifier is preferably polysorbate 60 or polysorbate 80.

Possibly, the pharmaceutical composition (or pharmaceutical kit of parts) further comprises additional ingredients, which inhibit pathways involved in cancer progression and kill cancer cells while ensuring a positive benefit/risk ratio to a patient.

Advantageously, this pharmaceutical composition (or kit of parts) is provided for use in the treatment of cancer e.g. inhibiting the growth and/or spread of a cancer.

A related (or combined) aspect of the present invention is thus a pharmaceutical kit of parts comprising at least three ingredients from a HMG-CoA reductase inhibitor, a leukotriene antagonist, a proton pump inhibitor, melatonin or a melatonin receptor agonist, (bioavailable) curcumin, a calciferol derivative, metformin or phenformin, valproate and/or valproic acid, minocycline, doxycycline and chloroquine; and one or more pharmaceutically acceptable carriers or excipients, wherein at least two of said at least three ingredients is selected from a HMG-CoA reductase inhibitor, a proton pump inhibitor, melatonin or a melatonin receptor agonist, (bioavailable) curcumin, a calciferol derivative and metformin (or phenformin).

Possibly, this pharmaceutical composition comprising a calciferol derivative and/or a (bioavailable) curcumin and/or melatonin (or a melatonin receptor agonist) is incorporated in a pharmaceutical kit of part further comprising a (one or more) compound from the group consisting of HMG-CoA reductase inhibitor, a leukotriene antagonist, a proton pump inhibitor, metformin or phenformin, as well as possibly valproate, minocycline and/or chloroquine, more preferably, this pharmaceutical kit further comprises metformin and/or an HGM-CoA reductase inhibitor and/or a proton pump inhibitor.

Preferably, this pharmaceutical composition, or pharmaceutical kit of parts, comprises at least three of (more preferably at least four of; still more preferably all the five) (a) a HMG-CoA reductase inhibitor, (b) melatonin or a melatonin receptor agonist, (c) (bioavailable) curcumin, (d) a calciferol derivative and (e) metformin or phenformin.

Alternatively, this pharmaceutical composition, or pharmaceutical kit of parts, comprises at least (i) melatonin (or a melatonin receptor agonist) and/or (bioavailable) curcumin, (ii) a calciferol derivative, and (iii) one or more ingredient(s) selected from the group consisting of a HMG-CoA reductase inhibitor, a leukotriene antagonist, a proton pump inhibitor, a compound selected from metformin, phenformin, valproate, minocycline and chloroquine.

Alternatively, this pharmaceutical composition, or pharmaceutical kit of parts, comprises at least (i) HMG-CoA reductase inhibitor, (ii) a calciferol derivative, and (iii) one or more ingredient(s) selected from the group consisting of melatonin (or a melatonin receptor agonist) and/or curcumin, a leukotriene antagonist, a proton pump inhibitor, a compound selected from metformin, phenformin, valproate, minocycline and chloroquine.

Alternatively, this pharmaceutical composition, or pharmaceutical kit of parts, comprises at least (i) HMG-CoA reductase inhibitor, (ii) a compound selected from melatonin (or a melatonin receptor agonist) and/or (bioavailable) curcumin, and (iii) one or more ingredients selected from the group consisting of a calciferol derivative a leukotriene antagonist, a proton pump inhibitor, a compound selected from metformin, phenformin, valproate, minocycline and chloroquine.

Alternatively, this pharmaceutical composition, or pharmaceutical kit of parts, comprises at least (i) metformin (or phenformin), (ii) a proton pump inhibitor and (iii) one or more ingredients selected from the group consisting of HMG-CoA reductase inhibitor, melatonin (or a melatonin receptor agonist), (bioavailable) curcumin, a calciferol derivative a leukotriene antagonist, valproate, minocycline and chloroquine.

Alternatively, this pharmaceutical composition, or pharmaceutical kit of parts, comprises at least (i) metformin (or phenformin), (ii) melatonin (or a melatonin receptor agonist), and (iii) one or more ingredients selected from the group consisting of a proton pump inhibitor, HMG-CoA reductase inhibitor, (bioavailable) curcumin, a calciferol derivative a leukotriene antagonist, valproate, minocycline and chloroquine.

Another related aspect of the present invention is a method of treating cancer in a patient in need thereof comprising administering to the patient an effective amount of a combination of active ingredients (in a pharmaceutical composition or in the pharmaceutical kit of parts) comprising at least three ingredients from a HMG-CoA reductase inhibitor, a leukotriene antagonist, a proton pump inhibitor, melatonin (or a melatonin receptor agonist), (bioavailable) curcumin, a calciferol derivative and a compound from the group consisting of metformin (or phenformin), valproate (and/or valproic acid), minocycline and chloroquine, and one or more pharmaceutically acceptable carriers or excipients, wherein at least two of said at least three ingredients is selected from a HMG-CoA reductase inhibitor, a leukotriene antagonist, a proton pump inhibitor, melatonin (or a melatonin receptor agonist), (bioavailable) curcumin, a calciferol derivative and a compound from the group consisting of metformin and phenformin.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention.

Definitions

The term "pharmaceutical", as used in disclosing the present invention, means relating to medicinal drugs and nutraceuticals for the treatment of mammals, or their preparation, use for humans and for veterinary use, or sale.

The term "nutraceutical" as used in disclosing the present invention, means referring to a product isolated or purified from foods that is generally sold in medicinal forms not usually associated with food. A nutraceutical is demonstrated to have a physiological benefit or provide protection against chronic disease.

The term "pharmaceutical composition", as used in disclosing the present invention, means a composition suitable for the treatment of mammals i.e. for human and veterinary use.

Statins (or HMG-CoA reductase inhibitors), as used in disclosing the present invention, means a class of drugs used to lower cholesterol levels by inhibiting the enzyme HMG-CoA reductase, which plays a central role in the production of cholesterol in the liver e.g. simvastatin, atorvastatin, fluvastatin, lovastatin, pitavastatin, pravastatin, and rosuvastatin.

A leukotriene antagonist (also referred to as a leukast), as used in disclosing the present invention, means a drug that inhibits leukotrienes, which are fatty compounds produced by the immune system that cause inflammation in asthma and bronchitis, and constrict airways e.g. montelukast, zafirlukast, Pranlukast and zileuton. Agents such as montelukast and zafirlukast block the actions of cysteinyl leukotrienes at the CysLT1 receptor on target cells such as bronchial smooth muscle.

Proton pump inhibitors (e.g. Omeprazole, Lansoprazole, Dexlansoprazole, Esomeprazole, Pantoprazole, Rabeprazole and Ilaprazole) act by irreversibly blocking the hydrogen/potassium adenosine triphosphatase enzyme system (the H+/K+ ATPase, or, more commonly, the gastric proton pump) of the gastric parietal cells.

VitaminD (or calciferol) is a group of fat-soluble secosteroids responsible for enhancing intestinal absorption of calcium and phosphate. In humans, the most important compounds in this group are vitamin D3 (Cholecalciferol) and vitamin D2 (ergocalciferol), which can be ingested from the diet and from supplements.

Acalciferol derivative, as used in the present invention, means a compound derived from calciferol e.g. alfacalcidol, calcifediol, calcitriol, cholecalciferol, ergocalciferol, 22-dihydroergocalciferol and sitocalciferol.

Metformin is N,N-Dimethylimidodicarbonimidic diamide.

Phenformin is 2-(N-phenethylcarbamimidoyl)guanidine.

Curcumin is also known as diferuloylmethane; curcumin I, C.I. 75300, and Natural Yellow 3 and has the IUPAC name of (1E,6E)-1,7-Bis(4-hydroxy-3-methoxyphenyl)-1,6-heptadiene-3,5-dione.

In the present invention, curcumin may also refer to a derivative of a curcumin with different chemical groups that have been formed to increase solubility and bioavailability of curcumin and make them suitable for drug formulation.

Bioavailability, as used in disclosing the present invention, means the releasability of a pharmaceutically relevant concentration of the active ingredient in plasma e.g. human or animal plasma.

Bioavailable curcumin refers to a curcumin derivative or, preferably, to curcumin formulated to increase its bioavailability (e.g. in a mixture with an about 6-fold mass excess of polysorbate 60 or 80).

In the present invention, the terms "curcumin", "(bioavailable) curcumin" and "bioavailable curcumin" refers to any composition comprising (a sufficient amount of) curcumin or a derivative thereof; provided that the anti-inflammatory and antioxidant properties of curcumin are substantially kept (at least 50% of the antioxidant activities are kept). Not-derivatised curcumin is among the preferred antioxidant and/or anti-inflammatory compounds of the present invention. A preferred curcumin composition is a mixture of curcumin with emulsifiers (such as polysorbate 60 or 80) in a weight excess so as to increase the bioavailability of curcumin.

Melatonin is N-[2-(5-methoxy-1H-indol-3-yl)ethyl]acetamide. Melatonin, beside its function of activating melatonin receptors, encompasses useful antioxidant properties. Melatonin and melatonin derivatives are added in the pharmaceutical composition and kit of parts of the present invention, for their capacity to activate melatonin receptors or for their antioxidant properties (for instance, an agonist of the melatonin receptor can be used, even if deprived of antioxidant function; conversely, an isomer of melatonin can be used for its antioxidant properties, even if its agonist function is strongly impaired; i.e. a 10-fold or even a 1000-fold reduced affinity), preferably for both. In the present invention, "melatonin" refers to any composition comprising (a sufficient amount of) melatonin or a derivative thereof, including agonists (such as agonists with improved pharmacokinetics properties) of the melatonin receptors MT1 and/or MT2, and mixture of melatonin and agonists of the melatonin receptors.

Metronomic therapy, as used in the present invention, is a continuous or frequent treatment with low doses of anti-cancer drugs, often given with other methods of therapy.

Maintenance chemotherapy, as used in the present invention, is a repeated low-dose treatment to prolong remission.

Combination chemotherapy, as used in the present invention, involves treating a patient with a number of different drugs simultaneously. The drugs differ in their mechanism and side effects. The biggest advantage is minimising the chances of resistance developing to any one agent. Also, the drugs can often be used at lower doses, reducing toxicity.

FOLFIRI is a chemotherapy regimen for the treatment of colorectal cancer. It is made up of the following drugs: FOL—folinic acid (leucovorin), a vitamin B derivative used as a "rescue" drug for high doses of the drug methotrexate and that modulates/potentiates/reduces the side effects of fluorouracil; F—fluorouracil (5-FU), a pyrimidine analog and antimetabolite which incorporates into the DNA molecule and stops synthesis; and IRI—irinotecan (Camptosar), a topoisomerase inhibitor, which prevents DNA from uncoiling and duplicating. Cetuximab, a monoclonal antibody to epidermal growth factor receptor or bevacizumab, a monoclonal antibody to vascular endothelial growth factor are sometimes added to FOLFIRI.

A carcinoembryonic antigen (CEA) test is a blood test used to help diagnose and manage certain types of cancers, especially cancer of the colon and of some lung cancers. The test measures the amount of CEA present in the blood. This test helps to determine if the treatment for the cancer is working (a reduction of the CEA level reflecting the efficacy of the treatment).

Screening of Drugs

Numerous molecular pathways operating differently in cancer and normal cells have been identified. Many currently marketed drugs (for other indications than cancer) are interfering with these pathways (several hundreds drugs identified by the inventor). Examples of low toxicity old drugs which have been reported in in vitro screening of drug library as potentially interfering with cancer together with the class of drugs to which they belong include:

histonedeacetylase inhibitors HDACi: Valproate, Valproic acid (anti-epileptic);

mitochondrial benzodiazepine receptors (MBDZR): diazepam (Valium) (anxiolytic);

PPAR-gamma agonists: glitazone (anti-diabetes 2);

COX-2 inhibitors (anti-inflammatory);
proteasome inhibitors: disulfiram (antabuse) (treatment of alcoholism);
NSAIDS: ibuprofen, indomethacin, aspirin, sulfalazine, paracetamol, diclofenac, ketoralac, naproxen, indometacin (anti-inflammatory);
HMG-CoA reductase inhibitor, statins: (anticholesterol);
PARP-1 inhibitors: minocycline (antibiotic);
biphosphonates (anti-osteoporosis);
Vitamin D, an immune booster which inhibits profilation of abnormal cells and acts as a classic steroid hormone;
SERMS (selective estrogen receptor modulators): raloxifene (anti-osteoporosis);
mifepristone (abortive pills);
beta-blockers (anti-hypertension);
Genisteine;
antiamebics e.g. fumagillin;
chlorpromazine+pentamidine
antimycotics e.g. ketoconazole
antibiotics e.g. doxycycline, clarithromycine
ACE inhibitors (anti-hypertension) e.g. perindopril, captopril, enalapril, lisinopril, and ramipril.
cardiotonic glycosides e.g. digitoxine, digoxine, ouabaine (one likely mechanism is glycolysis inhibition);
antidiabetic agents and mTOR signaling pathway blockers e.g. metformin and phenformin;
anti platelets aggregation agents e.g. dipyridamole;
melatonin;
anti-malarial agents e.g. chloroquine, hydroxychloroquine, artemether;
"antioxidants" e.g. curcumin and curcuminoids;
antihelminthics e.g. niclosamide.

Examples of higher toxicity drugs which have been reported as interfering with cancer together with the class of drugs to which they belong include:
mTOR inhibitors e.g. rapamycine (immunosuppressant);
retinoids e.g. ATRA (All Trans Retinoic Acid);
thalidomide.

A first selection was made by the inventor using the six criteria:
(1) unlikely to add severe side effects (well-known side effects pattern based on long use history);
(2) no aversive effect, no interaction with each other, compatible and possibly synergistic with chemotherapy, radiotherapy, surgery, immunotherapy, antiangiogenic and targeted therapy, while possibly improving tolerance to cancer therapies;
(3) clinical long term safety (most of the drug selected provide lifespan extension in animal models);
(4) target as many pathways (prevalent in many cancer, complementary, present in cancer stem cells) relevant to cancer patients as possible with the drugs selected, some drugs targeting multiple pathways;
(5) dose range of preclinical data close to clinical dose range;
(6) data available from epidemiological studies, from clinical trials for each drug separately.

Toxicity is the most important criterion. Long term tolerance is required without major side-effects. Evidence of non-interference with cancer therapy is also very important as is some evidence of anti-cancer activity.

Melatonin was well tolerated during an observation period of up to 2 years in a clinical safety study at a chronic high-dose (300 mg/day) rectal melatonin. Importantly, circulating serum protein carbonyls, which provide a surrogate marker for oxidative stress, were elevated in amyotrophic lateral sclerosis (ALS) patients, but were reduced to normal values by melatonin treatment. This combination of preclinical effectiveness and proven safety in humans suggests that high-dose melatonin is suitable for clinical trials aimed at neuroprotection through antioxidation in ALS. Therefore, melatonin can be safely incorporated in the selected formulation or pharmaceutical kit in a dose of about 20 mg per day (e.g. between 10 mg and 100 mg, preferably between 15 mg and 50 mg, more preferably between 20 mg and 40 mg) as in most cancer trials. In view of its sleep inducing properties, melatonin should be given 30 minutes before bedtime.

As statins are the most prescribed drugs, with few people experiencing major side-effects, they can be safely incorporated in the selected formulation. People intolerant to statins should take a selected formulation without statins.

Metformin has a very low toxicity profile (1000-2500 mg/d in standard non-cancer treatment), is compatible with chemotherapy, radiotherapy, surgery, immunotherapy, antiangiogenic and targeted therapy.

Therefore, metformin is a suitable drug to be mixed with other drugs of satisfactory profile in order to treat cancer patients regardless of the additional therapy administered. Metformin is safer than phenformin, and the risk of developing lactic acidosis is not increased by the medication as long as it is not prescribed to known high-risk groups. Therefore, metformin is preferred over phenformin, and can be incorporated in the pharmaceutical composition or pharmaceutical kit in the dose between 250 and 2000 mg/d.

Curcumin is the yellow pigment isolated from the rhizomes of *Curcuma longa*, commonly known as turmeric. Curcumin is a highly pleiotropic molecule with an excellent safety profile, and strong molecular evidence has been published for its potency to target multiple inflammatory diseases making it as a good candidate for the management of osteoarthritis due to safety profile and potential efficacy. Clinical studies of curcumin in humans with high doses (2-12 grams) have shown few side effects, with some subjects reporting mild nausea or diarrhea. Therefore, curcumin can be safely incorporated in the selected formulation. Possible means of improving the bioavailability of curcumin, include the use of adjuvant like piperine that interferes with glucuronidation, the use of liposomal curcumin, curcumin nanoparticles, the use of curcumin phospholipid complex and the use of structural analogues of curcumin. Using Flexofytol® (Tilman SA), which is a curcumin:polysorbate formulation, plasma concentrations of 190 ng/mL have been observed in humans, which is considerably greater than the 51.2 ng/mL reported in other studies aiming at improving curcumin bioavailability. Therefore the present pharmaceutical composition or kit can comprise a curcumin:edible emulsifier (e.g. polysorbate) composition (e.g. between 10 and 200 mg of curcumin and/or an amount to allow the administration to a human patient of between 20 and 400 mg per day, preferably between 20 and 100 mg, more preferably between 40 and 80 mg, and at least 6-time more of the edible emulsifier on a weight basis), such as the compositions described in WO 2010/106191.

Vitamin D toxicity is rare. The threshold for vitamin D toxicity has not been established, but the tolerable upper intake level (UL) is 4000 IU/day for ages 9-71. Vitamin D overdoses causes hypercalcemia. Published cases of toxicity involving hypercalcemia in which the vitamin D dose and the 25-hydroxy-vitamin D levels are known all involve an intake of at least 40,000 IU (1000 µg)/d. Therefore, Vitamin D can be safely incorporated in the pharmaceutical composition at a dose of 3500 IU (i.e. about 90 µg) per day.

Proton pump inhibitors (PPIs) rank as one of the safest classes of medications that gastroenterologists deal with, but reports of potential adverse effects associated with use of PPIs have emerged. Therefore, PPIs can be safely incorporated in the selected formulation at a dose of 20 to 80 mg/day.

Common side effects of leukotriene receptor antagonists are mild and include dyspepsia, abdominal discomfort, asthenia, headache, . . . . Leukotriene receptor antagonists can be safely incorporated in the selected formulation at a dose of 10 mg/day for Montelukast and 40 mg/day for Zafirlukast.

Valproate and valproic acid, could induce hepatic toxicity and/or thrombopenia in a small percentage of patients. However, they could be incorporated in the selected formulation for instance if a resistance to the other selected repurposed drugs appears: the inventor has found that they synergize for anticancer activity with metformin, melatonin, vitamin D, curcumin and statins.

Therefore, valproate and valproic acid can be incorporated in the selected formulation starting at a dose of 10 mg/kg. Their plasma concentration must be monitored and not be superior to 100 μg/ml.

Chloroquine could produce gastrointestinal side effects and reversible retinian deposit. Chloroquine at the doses used for prevention of malaria, produce side effects including gastrointestinal problems, stomach ache, itch, headache, postural hypotension, nightmares and blurred vision. However, the inventor has found that chloroquine has synergized with the other compounds (metformin, melatonin, vitamin D, curcumin and statins) in treating cancer.

Therefore, in spite of its higher toxicity, Chloroquine can be added to the selected formulation at a dose of 50 to 150 mg/day. It will be especially useful for treating clinical relapse.

The choice of further ingredients to the drug and nutraceutical cocktail is dictated by the incidence of possible side-effects.

Antibiotics include the macrolides, the tetracyclines e.g. minocycline, the quinolones and antimycotic drugs. Macrolides should only be incorporated in the selected formulation where their benefit/risk ratio is positive, because the combination of some macrolides and statins is not advisable and can lead to debilitating myopathy, while some macrolides (clarithromycin and erythromycin, not azithromycin) are potent inhibitors of the cytochrome P450 system, particularly of CYP3A4. Tetracyclines should be used with caution in those with liver impairment and those that are soluble in water and urine worsen renal failure.

Minocycline may cause upset stomach, diarrhea, dizziness, unsteadiness, drowsiness, mouth sores, headache and vomiting. Minocycline also increases sensitivity to sunlight and may affect quality of sleep and rarely cause sleep disorders. Minocycline, but not other tetracyclines, can cause vestibular disturbances with dizziness, ataxia, vertigo and tinnitus. However, the inventor has found that minocycline can be incorporated in the pharmaceutical composition or kit of part of the present invention as it has synergized with metformin, melatonin, vitamin D, curcumin and statins: in these specific conditions (in synergy with at least two compounds from the group consisting of metformin, melatonin, vitamin D and curcumin) the benefit of minocyclin clearly overweights its risk.

The other antibiotics should not be incorporated in the selected formulation, or only be incorporated in the selected formulation where their benefithisk ratio is positive.

Fluoroquinolones are generally well tolerated, with most side effects being mild to moderate. Some of the serious adverse effects that occur more commonly with fluoroquinolones than with other antibiotic drug classes include central nervous system (CNS) and tendon toxicity. The currently marketed quinolones have safety profiles similar to those of other antimicrobial classes.

Glucosamine in clinical studies has been consistently found to be safe, only exhibiting adverse effects, which are usually mild and infrequent, including stomach upset, constipation, diarrhea, headache and rashes.

Antimycotic drugs, i.e. any drug which destroys or prevents the growth of fungi, is one of the antibiotic groups. There are several classes of antifungal drugs: polyenes, which cause an increase in fungal cell wall permeability leading to its death e.g. amphotericin B, natamycin, nystatin; azoles, which act either by inhibiting the synthesis of ergosterol, a component of fungal cell wall or by causing direct wall damage e.g. clotrimazole, econazole, fluconazole, itraconazole, ketoconazole, miconazole; and pyrimidines, which interfere with the normal function of fungal cells e.g. flucytosine. Azoles have the following side-effects in at least one percent of patients: rashes, headache, dizziness, nausea, vomiting, abdominal pain, diarrhea, and/or elevated liver enzymes.

Mebendazole, an antihelminthic drug, is relatively free of toxic side effects or adverse reactions, although patients may complain of transient abdominal pain, heart pain, diarrhea, slight headache, fever, dizziness, exanthema, urticaria, and angioedema.

Niclosamide, also an antihelminthic drug, can have side effects such as abdominal pain, anorexia, diarrhea, and emesis. Rarely, dizziness, skin rash, drowsiness, perianal itching, and an unpleasant taste.

Antimalarial drugs all have unpleasant side-effects. Chloroquin, despite its side effects, can be incorporated to synergize (in synergy with at least two compounds from the group consisting of metformin, melatonin, vitamin D and curcumin; see above) with the other compounds of the pharmaceutical composition or kit of parts according to the present invention. Mefloquine can cause mental health problems, including anxiety, hallucinations, depression, unusual behavior, and suicidal ideations. The symptomatic adverse reactions produced by Artemether are more or less tolerable and if they become severe, they can be treated symptomatically, these include dizziness, headache, nausea and vomiting.

Metronidazole, an antiprotozoal drug also having an antabuse effect in association with alcohol, is very bitter and has a persistent metallic taste that causes loss of appetite and disgust for food. It can cause headaches. The long-term use and high doses can cause peripheral neuropathy.

Pentamidine, an antiPneumocystis Jiroveci drug, can cause allergic and toxic side effects, most commonly having effects on the pancreas, which in part depend on the daily and/or cumulative dose.

Antitoxoplasmosis drugs, such as pyrimethamine, may deplete folic acid in humans, resulting in the hematologic side effects associated with folate deficiency.

NK1 receptors antagonists, (aprepitant for example), due to their strong antiemetic efficacy that allows patients to tolerate emetic drugs, (like for instance chloroquine and/or disulfiram), and as tumour cells overexpress NK-1 receptors, which are involved in their viability, (NK-1 receptor antagonists, after binding to their molecular target, induce the death of tumour cells by apoptosis, exert an antiangiogenic action and inhibit the migration of tumour cells) should be incorporated in the selected formulation.

Other not Preferred Drugs:

Antiarythmics drugs should only be incorporated in the selected formulation (QT interval prolongation and torsade de pointe in addition to the same adverse effects as with beta-blockers) where their benefit/risk ratio is positive, as cancer patients during cancer therapy are very asthenic, anaemic and lipothymic.

Pulmonary hypertension drugs should only be incorporated in the selected formulation in the case of endothelin receptor antagonists where their benefit/risk ratio is positive, due to an increase of hepatic enzymes, anemia, oedema, Blurred vision, faintness or lightheadedness when getting up from a lying or sitting position, confusion, dizziness, dark urine, fever with or without chills, loss of appetite, nausea and vomiting, stomach pain, sudden sweating, unusual tiredness or weakness; and in the case of PDE5 inhibitors due to the occurrence of adverse drug reactions (ADRs) such as headaches, occurring in >10% of patients, dizziness, flushing, dyspepsia, nasal congestion, rhinitis and possible sudden hearing loss.

Low-molecular-weight heparins should only be incorporated in the selected formulation if hypercoagulability found sometimes in cancer patients and deep veinous thrombosis risk requires its usage or where their benefit/risk ratio is positive, since cancer patients very often have low platelets count during therapy and are at risk of bleeding.

Histamine(2) receptor antagonists should only be incorporated in the selected formulation where their benefit/risk ratio is positive for the following reasons: cimetidine may cause gynecomastia in males, loss of libido, and impotence and increase the risk of cognitive decline, but H2 antagonists are, in general, well tolerated, except for cimetidine.

Peripheralopiate agonists should only be incorporated in the selected formulation where their benefit/risk ratio is positive, due to adverse drug reactions (ADRs) associated with loperamide which include abdominal pain and bloating, nausea, vomiting and constipation.

PPAR-gamma agonists should only be incorporated in the selected formulation where their benefit/risk ratio is positive for the following reasons: risk of liver failure, water retention leading to oedema, increased risk of coronary heart disease. The main side effect of all thiazolidinediones is water retention, leading to edema, generally a problem in less than 5% of individuals, but a big problem for some and potentially, with significant water retention, leading to a decompensation of potentially previously unrecognized heart failure. Therefore, thiazolidinediones should be prescribed with both caution and patient warnings about the potential for water retention/weight gain, especially in patients with decreased ventricular function (NYHA grade III or IV heart failure).

NSAID's should only be incorporated in the selected formulation if hypercoagulability found sometimes in cancer patients and deep veinous thrombosis risk require its usage or where their benefit/risk ratio is positive, since cancer patients have very often low platelets count during therapy and are at risk of bleeding. Moreover, the risk of gastric irritation and bleeding is added to the one linked to the cancer therapy.

The side-effects of leflunomide affect quite a number of organ systems, are frequent and at times severe or even fatal and therefore, leflunomide should only be incorporated in the selected formulation where their benefit/risk ratio is positive.

As a mitotic inhibitor, colchicine should only be incorporated in the selected formulation where their benefit/risk ratio is positive, side-effects include gastrointestinal upset and neutropenia.

Allopurinol should only be incorporated in the selected formulation where its benefit/risk ratio is positive, since some patients are hypersensitive to the drug. Moreover, since allopurinol is not a uricosuric, it can be used in patients with poor kidney function and allopurinol has two important disadvantages: first, its dosing is complex and second, some patients are hypersensitive to the drug, therefore its use requires careful monitoring. Allopurinol has rare but potentially fatal adverse effects involving the skin.

Biphosphonates should only be incorporated in the selected formulation where their benefit/risk ratio is positive, since when administered intravenously for the treatment of cancer, it has been associated with osteonecrosis of the jaw. Moreover, oral bisphosphon-ates can cause upset stomach and inflammation and erosions of the esophagus, which is the main problem of oral N-containing preparations.

Selective oestrogen receptor modulators SERMS produce significantly more strokes and blood clots than the placebo and hence SERMS should only be incorporated in the selected formulation where their benefit/isk ratio is positive.

Adverse effects of benzodiazepines such as diazepam include anterograde amnesia and confusion (especially pronounced in higher doses) and sedation. Therefore, benzodiazepines should only be incorporated in the selected formulation where their benefit/risk ratio is positive.

Antidepressants should only be incorporated in the selected formulation where their benefit/risk ratio is positive, because of serious side effects. SSRIs inhibit serotonin-mediated platelet activation. This leads to increased risk of gastrointestinal bleeding. SSRI side effects include but are not limited to: Serotonin syndrome, nausea, diarrhea, increased blood pressure, agitation, headaches, anxiety, nervousness, emotional lability, increased suicidal ideation, suicide attempts, insomnia, drug interactions, neonate adverse reactions, anorexia, dry mouth, somnolence, tremors, sexual dysfunction, decreased libido, asthenia, dyspepsia, dizziness, sweating, personality disorder, epistaxis, urinary frequency, menorrhagia, mania/hypomania, chills, palpitations, taste perversion, and micturition disorder drowsiness, GI irregularities, muscle weakness, long term weight gain. With tricyclic antidepressants common side effects include: dry mouth, blurred vision, drowsiness, dizziness, tremors, sexual problems, skin rash, and weight gain or loss. Toxicity occurs at about ten times normal dosages; these drugs are often lethal in overdoses, as they may cause a fatal arrhythmia. However, tricyclic antidepressants are still used because of their effectiveness, especially in severe cases of major depression. With MAOIs (monoamine oxidase inhibitors) side effects include: a potentially lethal hypertensive reaction if taken with foods that contain excessively high levels of tyramine, such as mature cheese, cured meats or yeast extracts. Likewise, lethal reactions to both prescription and over the counter medications have occurred. Other side effects of MAOI include: hepatitis, heart attack, stroke, and seizures. Serotonin syndrome is a side-effect of MAOIs when combined with certain medications.

Pharmaceutical Composition and Pharmaceutical Kit of Parts

According to a first aspect of the present invention a pharmaceutical (human and veterinary) composition or a pharmaceutical kit of parts formulated for administration to a patient is provided comprising at least three ingredients from a HMG-CoA reductase inhibitor, a leukotriene antagonist, a proton pump inhibitor, melatonin or a melatonin receptor agonist, a bioavailable preparation of a curcuminoid, a calciferol derivative, a compound from the group consisting of metformin and phenformin, valproate, minocycline and chloroquine and one or more pharmaceutically acceptable carriers or excipients, wherein at least two of said at least three ingredients is selected from a HMG-CoA reductase inhibitor, a proton pump inhibitor, melatonin (or a melatonin receptor agonist), (bioavailable) curcumin, a calciferol derivative and metformin (or phenformin). To assist the patient in complying with any dosing regime these ingredients can be administered in a single formulation (e.g. single pill formulation, single capsule formulation, single parenteral formulation) or in several formulations each of which may comprise more than one ingredient.

Preferably, the HMG-CoA reductase inhibitor (statin) is selected from the group consisting of simvastatin, atorvastatin, fluvastatin, lovastatin, pitavastatin, pravastatin, and rosuvastatin, with atorvastatin and simvastatin being preferred and atorvastatin being particularly preferred.

Preferably, the leukotriene antagonist is selected from the group consisting of montelukast, zafirlukast, pranlukast and zileuton, with montelukast being preferred.

Also preferably the proton pump inhibitor is selected from the group consisting of omeprazole, lansoprazole, dexlansoprazole, esomeprazole, pantoprazole, rabeprazole and ilaprazole, with omeprazole, esomeprazole, and pantoprazole being more preferred.

Preferably, the calciferol derivative is selected from the group consisting of alfacalcidol, calcifediol, calcitriol, cholecalciferol (Vitamin D3), ergocalciferol, 22-dihydroergocalciferol and sitocalciferol with cholecalciferol being preferred. Alternatively the calciferol derivative can be Vitamin D, which is a group of fat-soluble secosteroids responsible for enhancing intestinal absorption of calcium and phosphate. Furthermore, Vitamin D can be administered in the form of a multivitamin cocktail provided that the multivitamin cocktail does not contain Vitamin B12 or folic acid.

The curcumin may be incorporated as such or together with other nutraceuticals provided that its mean peak value in the human serum is greater than 20 ng/mL with greater than 40 ng/mL being preferred and greater than 100 ng/mL being particularly preferred and greater than 250 ng/mL being especially particularly preferred.

Preferably, the pharmaceutical composition or kit of parts consists of cholecalciferol, melatonin (or a melatonin receptor agonist), bioavailable curcumin and pharmaceutically acceptable excipients.

Alternatively, the pharmaceutical composition or kit of parts consists of cholecalciferol, melatonin (or a melatonin receptor agonist), bioavailable curcumin, metformin and pharmaceutically acceptable excipients.

Advantageously, the pharmaceutical composition or kit of parts consists of cholecalciferol, melatonin (or a melatonin receptor agonist), bioavailable curcumin, metformin, a HMG-CoA reductase inhibitor (statin) and pharmaceutically acceptable excipients.

Preferably, the pharmaceutical composition (or kit of part) of the present invention excludes antihypertensive drugs and/or antiarythmic drugs and/or pulmonary hypertension drugs and/or low molecular weight heparins and/or histamine(2) receptor antagonists, and/or peripheral opiate agonists, and/or PPAR gamma agonists and/or NSAID's, and/or leflunomide, and/or colchicines, and/or allopurinol, and/or biphosphonates, and/or selective oestrogen receptor modulators, and/or benzodiazepines, and/or antipsychotic drugs, and/or antidepressant drugs.

Administration of the Pharmaceutical Composition

The pharmaceutical compositions according to the present invention may be formulated for administration to mammals, including human beings, for the treatment of any one of the diseases specified below.

Preferably a pharmaceutical composition of the present invention, whether comprising the at least three of a HMG-CoA reductase inhibitor (statin), a leukotriene antagonist, a proton pump inhibitor, melatonin (or a melatonin receptor agonist), bioavailable curcumin, a calciferol derivative, a compound from the group consisting of metformin and phenformin, valproate, minocycline and chloroquine, or in combination with another active ingredient as specified hereinabove, may be used for the treatment and/or prophylaxis of cancer.

The pharmaceutical compositions of the present invention may be advantageously obtained in various forms, such as, for example, injectable or drinkable solutions, sugar-coated tablets, ordinary tablets or capsules e.g. gelatin. The suitable dosage can vary within a wide range depending on the base patient's age, weight and state of health, the nature and severity of the disease, as well as on the route of administration.

If Vitamin D (calciferol derivative) is present in the pharmaceutical composition, according to the present invention, the dosage thereof is preferably 10000 to 28000 UI (250 to 700 µg)/week, which can be provided in tablet form, in a capsule or as a solution in liquid carrier.

If melatonin is present in the pharmaceutical composition formulated for administration to a patient, according to the present invention, the dosage thereof is preferably 10 to 100 mg/d, which is generally available in tablet form.

If a curcuminoid is present in the pharmaceutical composition formulated for administration to a patient of average weight e.g. 75 kg, according to the present invention, the dosage thereof is 20 to 460 mg/d, which is generally available in tablet or in a capsule form.

If metformin or phenformin is present in the pharmaceutical composition formulated for administration to a patient of average weight e.g. 75 kg, according to the present invention, the dosage thereof is preferably 250 to 2500 mg/d.

If a statin is present in the pharmaceutical composition formulated for administration to a patient of average weight e.g. 75 kg, according to the present invention, the dosage thereof is preferably 10 to 80 mg/d.

If a leukotriene antagonist is present in the pharmaceutical composition formulated for administration to a patient of average weight e.g. 75 kg, according to the present invention, the dosage thereof is preferably 5 to 40 mg/d (e.g. 10 mg/day for montelukast and 40 mg/day for zafirlukast), with 10 to 30 mg/d being particularly preferred.

If a proton pump inhibitor is present in the pharmaceutical composition formulated for administration to a patient of average weight e.g. 75 kg, according to the present invention, the dosage thereof is preferably 10 to 160 mg/day, with 20 to 100 mg/day being particularly preferred.

While it is possible for the active ingredients to be administered alone and in different delivery forms it is preferable to present them as pharmaceutical formulations either continuously or discontinuously at more or less regular time intervals.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

When a solid composition in tablet form is prepared, the active ingredient or ingredients may be mixed with one or more pharmaceutically acceptable vehicles or excipients such as, but not limited to, gelatine, starch, lactose, magnesium stearate, talc, Gum Arabic or the like. The tablets can be coated with sucrose or other suitable materials, or, alternatively, they can be treated such that they have sustained or delayed activity and such that they release a predetermined amount of active principle continuously. A preparation in capsules is obtained by mixing the active ingredient with a diluent and by pouring the mixture obtained into soft or hard capsules. The water-dispersible powders or granules can contain the active ingredient mixed with dispersing agents or wetting agents, or with suspension agents, such as polyvinylpyrrolidone, as well as with sweeteners or flavour enhancers.

For rectal administration, use is made of suppositories which are prepared with binders which melt at the rectal temperature, for example cocoa butter or polyethyleneglycols.

For parenteral, intranasal or intraocular administration, aqueous suspensions, isotonic saline solutions or sterile injectable solutions which contain pharmacologically compatible dispersing agents and/or wetting agents, for example propylene glycol or polybutylene glycol are used.

For transmucous administration, the active principle or principles can be formulated in the presence of the promoter such as bile salt, hydrophilic polymer, such as, for example, hydroxypropylcellulose, hydroxypropylmethylcellulose, hydroxyethyl-cellulose, ethylcellulose, carboxymethylcellulose, dextran, polyvinylpyrolidinone, pectins, starch, gelatine, casein, acrylic acids, acrylic esters and copolymers thereof, vinyl polymers or copolymers, vinyl alcohols, alkoxy polymers, polyethylene oxide polymers, polyethers or mixtures thereof.

The active principle or principles can also be formulated in the form of microcapsules, optionally with one or more carriers or additives.

Use in the Treatment of Cancer

According to a related aspect of the present invention, the pharmaceutical composition or kit of parts according to the present invention is for use in cancer therapy e.g. reduction in pain, inhibiting the growth of a cancer, the cancer being preferably selected from the group consisting of group consisting of brain cancer, breast cancer, cervical cancer, colon cancer, gastric cancer, kidney cancer, leukemia, liver cancer, lung cancer, lymphoma, ovarian cancer, pancreatic cancer, prostate cancer, rectal cancer, sarcoma, skin cancer, testicular cancer, or uterine cancer with lung cancer and colon cancer being particularly preferred.

According to another related aspect of the present invention, the pharmaceutical composition or kit of parts according to the first aspect of the present invention is for prophylactic use against cancer or neurodegenerative conditions. For example this pharmaceutical composition or kit of parts is a combination of Vitamin D (e.g. chlolecalciferol), bioavailable curcumin and melatonin (or a melatonin receptor agonist) with pharmaceutically acceptable excipients. Preferably, this pharmaceutical composition or kit of parts further comprises minocycline and/or a statin.

Pharmaceutical Kit of Parts

In view of the fact that, when several active ingredients are used in combination, they do not necessarily bring out their joint therapeutic effect directly at the same time in the mammal to be treated, the corresponding composition may also be in the form of a medical kit or package containing the ingredients in separate but adjacent repositories or compartments. In the latter context, each active ingredient may therefore be formulated in a way suitable for an administration route different from that of the other e.g. some of them may be in the form of an oral or parenteral formulation whereas the other ingredients are in the form of an ampoule for intravenous injection or an aerosol.

According an aspect of the present invention a pharmaceutical kit of parts is provided comprising as active ingredients at least three of a HMG-CoA reductase inhibitor, a leukotriene antagonist, a proton pump inhibitor, melatonin (or a melatonin receptor agonist), bioavailable curcumin, a calciferol derivative, metformin (or phenformin), valproate, and one or more pharmaceutically acceptable carriers or excipients e.g. a pharmaceutical pack. The parts making up the pharmaceutical kit can be the individual active ingredients or combinations thereof and can be provided in different forms.

LEGEND OF THE FIGURE

The FIGURE is a PET scan of the patient of Example 1 on day 6, day 70 and day 232.

EXAMPLES

Example 1

Pharmaceutical composition I consisting of:
Cholecalciferol (Vitamin D3) (D-CURE from SMB Technology, S.A., 39 rue du Parc Industriel, B-6900 Marche-en-Famenne, Belgium) 25000 UI/week
Melatonin 20 mg/day
Pantoprazole 20 mg/day
Atorvastatin 10 mg/day
Metformin 500 mg/day
Curcumin 84 mg/day by taking Flexofytol® (produced by Tilman SA, Zl Sud 15, B-5377 Baillonville) 2 capsules/day
Was administered to patient A, a 69 year-old patient with advanced Non Small Cell Lung Cancer (NSCLC with wild type EGFR and ALK) resistant to chemotherapy (cisplatin and docetaxel); in such cancer survival is only a few months.
Patient Clinical Story:
Day 1 CEA 118 ng/ml treatment with composition 1 started
Day 6 PETSCAN (See the FIGURE): numerous hypermetabolic masses in left lung
(Standart Uptake Value SUVmax of the main lesion: 18.95), in the mediastin and the retro-laryngeal area.
Day 20 CEA 94 ng/ml
Thus, in absence of any other treatment than composition 1, the CEA decreased from 118 ng/ml to 94 ng/ml in 20 days, demonstrating an objective response due to composition 1.

On Day 20, chemotherapy cisplatin docetaxel is initiated; treatment with composition 1 stopped, patient hospitalized due to complications of chemotherapy Day 43 CEA 94 ng/ml no response to chemotherapy treatment composition 1 reinitiated for 5 days Day 48 second cure cisplatin docetaxel treatment with composition 1 stopped Day 56 CEA 88 ng/ml Thus, upon 36 days of chemotherapy, no objective efficient response could be demonstrated, (the inventor has subsequently attributed the small drop in CEA from 94 ng/ml to 88 ng/ml to the 5 days of composition 1 treatment).

Day 61 treatment composition 1 reinitiated

Day 70 PETSCAN (see the middle panel of the FIGURE) some improvement SUV of the main lesion: 8.6

Thus, upon 34 days of composition 1 treatment over a period of 70 days (treatment interrupted 36 days due to side effects of inefficient chemotherapy), the SUV of the main lesion dropped from 18.95 to 8.6, demonstrating at the imaging level an objective response to composition 1.

Day 73 CEA 84 ng/ml

In order to overcome an eventual resistance, it is decided to add Depakine, then minocycline to composition 1.

Day 79 Depakine (valproate 87 mg/day, valproic acid 200 mg/day) added to treatment Day 91 CEA 64 ng/ml Thus, Depakine has synergized with composition 1 and the CEA decreased from 84 ng/ml to 64 ng/ml in 12 days.

Day 98 Minocycline 100 mg/day added to the treatment

Day 104 CEA 54 ng/ml. This was accompanied by a decrease in pain quantified by a reduction in the dose of painkillers required.

Day 125 Radiotherapy 66 Gy during 6 weeks

Day 150 CEA 118 ng/ml (increase due to tumor necrosis induced by radiotherapy)

Day 168 end of radiotherapy

Day 195 CEA 65 ng/ml treatment composition 1 reinitiated

Day 231 CEA 31 ng/ml

Day 232 PETSCAN (see the right panel of the FIGURE): SUV of the main lesion: 3.9 improvement of the irradiated zone but apparition of small hypermetabolic spots in the supraclavicular area, Chloroquine 100 mg/day added to the treatment Day 265 CEA 17 ng/ml Day 279 CEA 12.4 ng/ml chemotherapy with pemetrexed started, treatment with composition 1 stopped Day 300 CEA 12 ng/ml no decrease with pemetrexed, treatment composition 1 reinitiated Day 301 PETSCAN SUV 4.1 disappearance of the supraclavicular hypermetabolic spots Day 314 CEA 9.7 complete disappearance of the pain This example shows that a composition comprising Cholecalciferol, curcumin and/or melatonin and compounds such as proton pump inhibitors and metformin synergizes with standard cancer therapies (radiotherapy) and chloroquine, minocycline and valproate.

Example 2

Patient 77 years old with advanced prostate cancer, progressing, (PSA increasing from 5.57 to 10.12 in 40 days) under therapy with histreline acetate subcutaneous implant, (gonadoreline analogue suppressing production of FSH and LH.).

Day 1 PSA: 10.12 ng/ml pharmaceutical composition 1 initiated

Day 100 PSA: 4.63 ng/ml

Thus composition 1 on its own is able to stop progression of a prostate cancer resistant to histreline and to induce a regression of the serological cancer marker.

Day 157 PSA: 11.44 ng/ml relapse, Chloroquine 100 mg/day added

Day 178 PSA: 9.88 ng/ml Enzalutamide (anti-androgen) added

Here also chloroquine was able to induce regression in a cancer relapsing while on treatment with composition 1 (cfr example 1).

Day 312 PSA: 0.90 ng/ml

Day 407 PSA: 0.40 ng/ml

This example shows that chloroquine synergizes with a composition comprising Cholecalciferol, curcumin and/or melatonin and compounds such as proton pump inhibitors and metformin and with enzalutamide.

Example 3

Patient, 76 years old, treated for transitional cell bladder carcinoma.

Before the treatment with composition 1 (without metformin), the patient was enduring local relapses (3 relapses in 2 years).

Since the treatment with composition 1 (without metformin), he has not experienced any single relapse for the last 3 years.

This example shows that the composition according to the present invention is effective per se.

Example 4

Pharmaceutical composition 1 was administered daily to patient D, a 36 year-old patient with stage IV advanced colon cancer, together with FOLFIRI (irinotecan 180 mg/m$^2$ body surface area, folinic acid 400 mg/m$^2$ body surface area, 4-fluoro-uracil 400 mg/m$^2$ body surface area as a bolus, 2000 mg/m$^2$ body surface area) as a 46 hour perfusion and bevacizumab as therapy.

Prior to starting administration of Pharmaceutical composition 1 in addition to the FOLFIRI and bevacizumab treatment, the CEA (carcino embryonic antigen) level was greater than 40 ng/ml. Four months after starting administration of pharmaceutical composition I the CEA level had decreased to 3 ng/ml. Moreover, during the therapy, when the FOLFIRI and bevacizumab treatment was interrupted because of toxicity or severe pyelonephritis, treatment with Pharmaceutical composition I was continued and a CEA drop was also observed during this period. From June 2013 to November 2013, the CEA level remained constant at 3 ng/ml and computed tomography, (CT-Scans), and positron emission tomography, (PET-Scans), confirmed complete remission.

From the review of the scientific literature, less than 10% of stage IV colon carcinoma patients are achieving complete remission upon therapy with FOLFIRI and bevacizumab.

This example shows that the composition according to the present invention is effective on its own, and furthermore, synergistic with standard cancer therapies.

Example 5

56 years old patient with advanced (stage III b, T2N1M0) epidermoid adenocarcinoma of the cervix in complete remission at two years after therapy with composition 1 and standard chemoradiotherapy.
From the review of the scientific literature, less than 40% of advanced (stage III b, T2N1M0) epidermoid adenocarcinoma of the cervix patients are achieving complete remission upon standard chemoradiotherapy.

Example 6

A patient suffering of NSCL has been given a treatment based on composition 1, a calciferol derivative, melatonin, curcumin and metformin, then supplemented with valproate, minocycline, chloroquine and disulfiram. Due to digestive problems resulting from her radiotherapy (the oesophagus was included in the irradiated field), she did not tolerate anymore the combined treatment. As she was relapsing after 2 years, (her CEA level was increasing from 40 ng/ml up to 90 ng/ml in 4 months), thereafter, the inventor has provided her the same treatment (with disulfiram but without chloroquine) together with aprepitant, this treatment was tolerated, and the CEA level dropped to 84 ng/ml in 21 days.
Thus, in a patient suffering of NSCLC, resistant to multiple chemotherapy, composition 1 with the addition of aprepitant (a neurokinin-1 receptor antagonist inhibiting the Wnt pathway active in multiple cancer) and disulfiram (a proteasome inhibitor) reverses the progression of multiresistant cancer.

The invention claimed is:

1. A pharmaceutical composition or a pharmaceutical kit of part comprising melatonin and/or curcumin, a calciferol derivative, and one or more compounds selected from the group consisting of an HMG-CoA reductase inhibitor, a proton pump inhibitor, metformin, phenformin, valproate, minocycline and chloroquine.

2. The pharmaceutical composition or the pharmaceutical kit of part of claim 1, comprising melatonin and/or curcumin, a calciferol derivative, an HMG-CoA reductase inhibitor, and one or more compounds selected from the group consisting of a proton pump inhibitor, metformin, phenformin, valproate, minocycline and chloroquine.

3. The pharmaceutical composition or the pharmaceutical kit of part of claim 1 comprising melatonin and/or curcumin, a calciferol derivative, chloroquine, and one or more compounds selected from the group consisting of an HMG-CoA reductase inhibitor, a proton pump inhibitor, metformin, phenformin, valproate and minocycline.

4. The pharmaceutical composition or the pharmaceutical kit of part according to claim 1, comprising melatonin and/or curcumin, a calciferol derivative, metformin, and one or more compounds selected from the group consisting of an HMG-CoA reductase inhibitor, a proton pump inhibitor, chloroquine, valproate and minocycline.

5. The pharmaceutical composition or the pharmaceutical kit of part according to claim 1, comprising melatonin and curcumin.

6. The pharmaceutical composition or the pharmaceutical kit of part according to claim 1, further comprising a leukotriene antagonist.

7. The pharmaceutical composition or the pharmaceutical kit of part according to claim 1, comprising between 10 mg and 100 mg/d of melatonin, and/or between 20 and 400 mg/d of curcumin and/or between 250 and 2000 mg/d of metformin, preferably wherein said curcumin is present in the said composition together with an at least 6-time mass excess of an edible emulsifier.

8. The pharmaceutical composition or the pharmaceutical kit of part according to claim 1, comprising a calciferol derivative, melatonin, curcumin, metformin and another compound selected from the group consisting of an HMG-CoA reductase inhibitor, a proton pump inhibitor, valproate, minocycline and chloroquine.

9. The pharmaceutical composition or the pharmaceutical kit of part according to claim 1, comprising a calciferol derivative, melatonin, curcumin, metformin, an HMG-CoA reductase inhibitor and another compound selected from the group consisting of a proton pump inhibitor, valproate, minocycline and chloroquine.

10. The pharmaceutical composition or the pharmaceutical kit of part according to claim 1, wherein the HMG-CoA reductase inhibitor is selected from the group consisting of simvastatin, atorvastatin, fluvastatin, lovastatin, pitavastatin, pravastatin, and rosuvastatin.

11. The pharmaceutical composition or the pharmaceutical kit of part according to claim 1, wherein the proton pump inhibitor is selected from the group consisting of omeprazole, lansoprazole, dexlansoprazole, esomeprazole, pantoprazole, rabeprazole and ilaprazole.

12. The pharmaceutical composition or the pharmaceutical kit of part according to claim 1, wherein the calciferol derivative is selected from the group consisting of alfacalcidol, calcifediol, calcitriol, cholecalciferol, ergocalciferol, 22-dihydroergocalciferol and sitocalciferol.

13. The pharmaceutical composition or the pharmaceutical kit of part according to claim 1, further comprising a proteasome inhibitor such as disulfiram.

14. The pharmaceutical composition or the pharmaceutical kit of part according to claim 1, further comprising aprepitant.

15. A method for the treatment of cancer, comprising:
administering to a subject in need thereof a pharmaceutical composition according to claim 1 for treatment of a cancer selected from the group consisting of brain cancer, breast cancer, cervical cancer, colon cancer, gastric cancer, kidney cancer, leukemia, liver cancer, lymphoma, lung cancer, ovarian cancer, pancreatic cancer, prostate cancer, rectal cancer, sarcoma, skin cancer, testicular cancer, and uterine cancer.

16. A pharmaceutical kit of parts comprising at least three ingredients from a HMG-CoA reductase inhibitor, a leukotriene antagonist, a proton pump inhibitor, melatonin, curcumin, a calciferol derivative, metformin, valproate, minocycline, doxycycline and chloroquine; and one or more pharmaceutically acceptable carriers, wherein at least two of said at least three ingredients is selected from a HMG-CoA reductase inhibitor, a proton pump inhibitor, melatonin, curcumin, a calciferol derivative and metformin.

17. A method of treating a cancer selected from the group consisting of brain cancer, breast cancer, cervical cancer, colon cancer, gastric cancer, kidney cancer, leukemia, liver cancer, lymphoma, lung cancer, ovarian cancer, pancreatic cancer, prostate cancer, rectal cancer, sarcoma, skin cancer, testicular cancer, and uterine cancer, comprising
administering to a subject in need thereof a pharmaceutical composition comprising melatonin and/or curcumin, a calciferol derivative, and one or more compounds selected from the group consisting of an HMG-CoA reductase inhibitor, a proton pump inhibitor, metformin, phenformin, valproate, minocycline and chloroquine.

18. The method according to claim 17, wherein the calciferol derivative is selected from the group consisting of alfacalcidol, calcifediol, calcitriol, cholecalciferol, ergocalciferol, 22-dihydroergocalciferol and sitocalciferol;
- the HMG-CoA reductase inhibitor is selected from the group consisting of simvastatin, atorvastatin, fluvastatin, lovastatin, pitavastatin, pravastatin, and rosuvastatin; and
- the proton pump inhibitor is selected from the group consisting of omeprazole, lansoprazole, dexlansoprazole, esomeprazole, pantoprazole, rabeprazole and ilaprazole.

19. The method according to claim 17, wherein the pharmaceutical composition comprises melatonin and curcumin.

20. The method according to claim 17, wherein the pharmaceutical composition is the sole cancer therapy administered to the subject.

* * * * *